(12) United States Patent
Daitch et al.

(10) Patent No.: US 7,998,731 B2
(45) Date of Patent: Aug. 16, 2011

(54) PORTABLE SAMPLING DEVICE FOR AIRBORNE BIOLOGICAL PARTICLES

(75) Inventors: Charles Daitch, Ann Arbor, MI (US);
Roger Reynolds, Charlottesville, VA (US); Stephen C. Francesconi, Washington, DC (US); Bouvard Hosticka, Charlottesville, VA (US); Kathy Terlesky, Charlottesville, VA (US); Eric J. Van Gieson, Charlottesville, VA (US)

(73) Assignee: General Dynamics Advanced Information Systems, Inc., Fairfax, VA (US)

( * ) Notice: Subject to any disclaimer, the term of this patent is extended or adjusted under 35 U.S.C. 154(b) by 1969 days.

(21) Appl. No.: 10/388,760

(22) Filed: Mar. 17, 2003

(65) Prior Publication Data
US 2004/0185554 A1    Sep. 23, 2004

(51) Int. Cl.
*C12M 1/26* (2006.01)
*C12M 3/00* (2006.01)
*G01N 1/22* (2006.01)

(52) U.S. Cl. ............ 435/309.1; 435/30; 435/287.6; 435/287.4; 435/288.3; 435/288.5; 435/808; 73/61.63; 73/863.23; 73/28.01; 73/28.04; 73/28.05; 73/863.21; 73/863.24

(58) Field of Classification Search .......... 435/30, 435/287.6, 287.4, 288.3, 288.5, 808, 309.1; 73/61.63, 863.23, 28.01, 28.04, 28.05, 863.21, 73/863.24
See application file for complete search history.

(56) References Cited

U.S. PATENT DOCUMENTS

| | | | |
|---|---|---|---|
| 3,748,905 A * | 7/1973 | Fletcher et al. | ............ 73/863.25 |
| 4,079,628 A | 3/1978 | Distenfeld et al. | |
| 4,080,832 A | 3/1978 | Moody et al. | |
| 4,389,903 A | 6/1983 | Bertone et al. | |
| 4,569,235 A | 2/1986 | Conkle et al. | |
| 4,761,639 A | 8/1988 | Pyke et al. | |
| 4,926,679 A | 5/1990 | Dewhurst | |
| 5,001,463 A | 3/1991 | Hamburger | |
| 5,107,713 A | 4/1992 | Peck et al. | |
| 5,395,426 A | 3/1995 | Huckins et al. | |
| 5,551,283 A | 9/1996 | Manaka et al. | |
| 5,551,311 A | 9/1996 | Ogden et al. | |
| 5,553,508 A | 9/1996 | Dabberdt et al. | |
| 5,574,230 A | 11/1996 | Baugh | |
| 5,646,357 A | 7/1997 | Ogden et al. | |
| 5,693,895 A | 12/1997 | Baxter | |
| 5,710,380 A | 1/1998 | Talley et al. | |
| 5,809,185 A * | 9/1998 | Mitchell | ............ 385/12 |
| 5,861,053 A | 1/1999 | Noritake et al. | |
| 5,904,752 A | 5/1999 | Willeke | |
| 5,919,576 A | 7/1999 | Hui et al. | |
| 6,087,183 A | 7/2000 | Zaromb | |

(Continued)

FOREIGN PATENT DOCUMENTS

CA    991562    6/1976

(Continued)

OTHER PUBLICATIONS

I. Gill, A. Ballesteros, "Encapsulation of Biologicals within Silicate, Siloxane, and Hybrid Sol-Gel Polymers: An Efficient and Generic Approach," J. Am. Chem. Soc. 1998, 120, p. 8587-8598.*

(Continued)

*Primary Examiner* — Nathan A Bowers
(74) *Attorney, Agent, or Firm* — Ingrassia Fisher & Lorenz, P.C.

(57) ABSTRACT

The present invention relates to a collection device for a substance, and methods related to collecting thereof.

25 Claims, 9 Drawing Sheets

U.S. PATENT DOCUMENTS

| | | |
|---|---|---|
| 6,105,440 A | 8/2000 | Lawless |
| 6,125,709 A | 10/2000 | Van Der Maas |
| 6,192,767 B1 | 2/2001 | Fiorina |
| 6,244,117 B1 | 6/2001 | Mengel et al. |
| 6,327,918 B1 | 12/2001 | Lawless |
| 6,422,061 B1 | 7/2002 | Sunshine et al. |
| 2001/0029793 A1 | 10/2001 | Moler et al. |
| 2002/0098097 A1 | 7/2002 | Singh |
| 2002/0098122 A1 | 7/2002 | Singh et al. |
| 2003/0008341 A1* | 1/2003 | Spurrell .......................... 435/34 |

FOREIGN PATENT DOCUMENTS

| | | |
|---|---|---|
| EP | 0777858 | 6/1997 |
| WO | WO 02/057744 A2 | 7/2002 |

OTHER PUBLICATIONS

U.S. Appl. No. 60/375,905, filed May 1, 2002.

U.S. Appl. No. 60/375,790, filed Apr. 16, 2002.

* cited by examiner

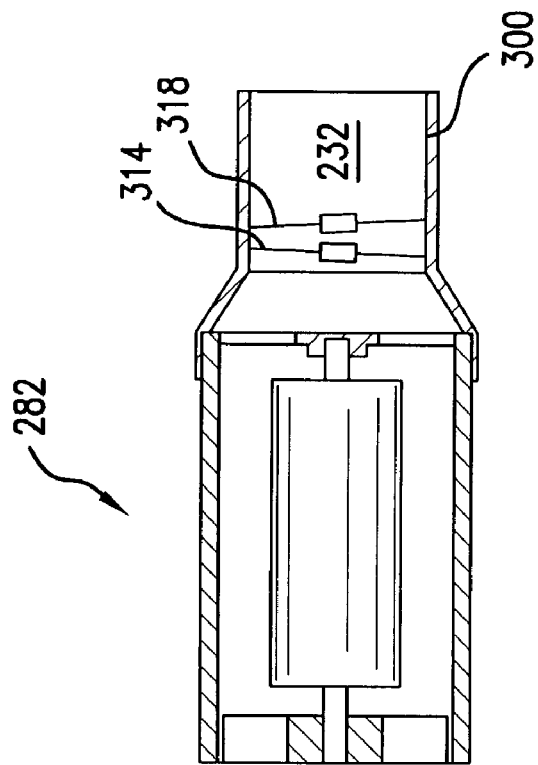
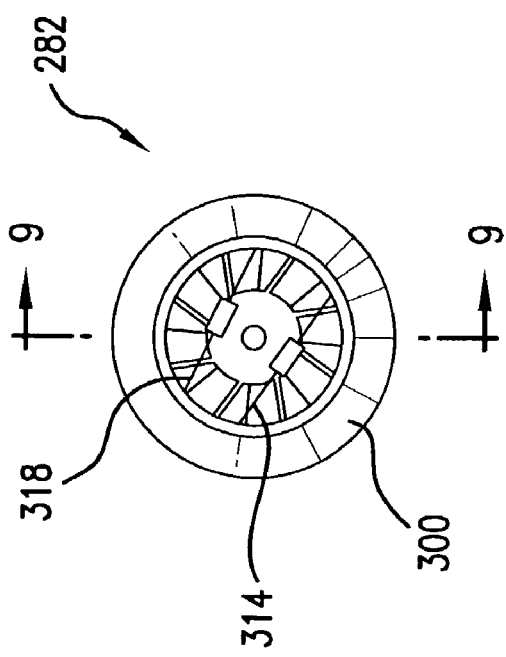
FIG.9
FIG.8

PORTABLE SAMPLING DEVICE FOR AIRBORNE BIOLOGICAL PARTICLES

GOVERNMENT LICENSE RIGHTS

The invention was made with government support under contract numbers N00173-02-P-0314, dated Jan. 25-Apr. 30, 2002; N00173-02-P-0513, dated Mar. 19-Apr. 30, 2002, N00173-02-P-0885, dated May 31-Aug. 31, 2002; N00173-02-F-1025, dated Sep. 13-Dec. 31, 2002, N00173-02-C-2010, dated Mar. 7, 2002, and N00173-99-C-2036. The government has certain rights in this invention.

The present invention generally relates to a collection and/or detection device for a substance, or a system or method for collecting a substance.

Recently, there are concerns about the release of harmful substances such as poisonous gas and/or pathogens by rogue nations or terrorists. To defend against these harmful substances, it is often beneficial to determine the identity of the released toxic organism and the extent of the infected area by sampling. Sampling devices can include impaction samplers that operate by directing a high-velocity air stream to a surface perpendicular to the direction of airflow; impinger samplers that involve passing air into a liquid media to collect spores and particles; filtration samplers that have a matrix of woven fabric to entrap particles from the inlet air, and cyclone devices which capture substances into a buffer using centrifugal force.

In one particular application, it is desirable to combine a detection sampler with an unmanned aircraft or unmanned aerial vehicle (UAV). Recent advances with unmanned aircraft miniaturization permit flying a relatively small aircraft from a remote location. It would be highly desirable to combine such a miniaturized aircraft with a suitable sampler to permit its transport by the aircraft.

Existing samplers suffer from several disadvantages. Impaction samplers are generally designed for a given air velocity to collect a relatively small range of particle sizes and, therefore, generally require modifications between sampling trials. Impinger samplers are generally monitored frequently to ensure that an adequate amount of liquid is available for particle entrapment, are difficult to miniaturize, and are limited to relatively low flow rates. Filtration samplers offer slightly higher collection efficiencies as compared to these other methods, however, they require higher driving pressure to achieve a desired flow rate, which results in a larger and heavier air handling system. Filtration samplers are also not compatible with some post-collection analysis techniques. There is a desire to provide a collection system for capturing harmful substances with a relatively small collection device.

SUMMARY OF THE INVENTION

One exemplary embodiment of the present invention can provide a portable collection device for a substance. Generally, the portable collection device includes a body, optionally rigid, forming a conduit for a gas, optionally throughout the length of the portable collection device, and a gas flow regulator for substantially blocking the flow of the gas through the conduit of the portable collection device thereby preventing sampling.

Another exemplary embodiment of the present invention may be a collection device for a substance. Generally, the device can include a first gas flow regulator and a second gas flow regulator generally aligned along a flow path of a gas passing through the collection device.

Still another exemplary embodiment of the present invention can be a method for retrieving a sample of a substance and minimizing exposure to the substance. The method may include removing a cartridge adapted to be removed in a conveniently releasable fashion from a collection device, and optionally reattachable in a conveniently attachable fashion. The cartridge may also include a collection material. In addition, the method generally also includes attaching at least one adapter to the cartridge that is conveniently releasable from the cartridge to permit washing the collection material.

A further exemplary embodiment of the present invention is a method of calculating a mass gas flow rate through a collection device. The method may include calculating a heat transfer coefficient from at least one measured parameter and correlating the calculated heat transfer coefficient to a mass gas flow rate value. The calculated mass gas flow rate values can then be stored in a microprocessor in the collection device.

Still yet another exemplary embodiment of the present invention is a collection device for a substance. The collection device may include a first cartridge having a collection material and a gas flow regulator. Generally, a gas entering the collection material is generally aligned with and in the same general gas flow path as a gas exiting the gas flow regulator.

Additionally, a collection device may include a nozzle, a first gas flow regulator, a second gas flow regulator, at least one instrument, a microprocessor, and an exhaust duct. Generally, the first gas flow regulator is a valve, a gas flow path through the collection device is generally linear after entering the nozzle and before exiting the exhaust duct, and at least one instrument provides at least one parameter for calculating the mass gas flow rate. A plurality of varying mass gas flow rates can be stored in the microprocessor.

The present invention can provide a collection device having a compact size to permit a variety of uses including its combination with a miniaturized unmanned aircraft, although the collection device can be transported by a variety of mechanisms, including by a person, land transport, or other air vehicles while sampling, or used while stationary. Furthermore, the device of the present invention can include beads coated with a glygel material to permit the collection of harmful substances during operation, e.g., flight. In addition, the present invention includes a valve for starting and stopping the collection of harmful substances to control the collection of substances in a predetermined area of interest. Moreover, the present invention provides a unique control scheme for recording variable mass gas flow rates passing through the device. Although one preferred usage for the collection device is sampling pathogens in air, it should be understood that the device of the present invention can be used to sample substances, harmful or otherwise, in other gas environments. Furthermore, gas or gas environments include liquids or solids suspended in at least one gas, such as smoke or dust, i.e. a solid aerosol, or a cloud, mist or fog, i.e. a liquid aerosol.

As defined herein, the term "portable" means that the device can be easily carried or moved in such a manner as not requiring significant severance or no severance from its surrounding support structure. As an example, such severance can be accomplished by the removal of several, e.g. not more than six, such as two, mechanical fasteners, so a user can move the device to a new location.

FIG. 8 is an elevational, end view of an exemplary exhaust duct with a motor of the present invention in view.

FIG. 9 is a cross-sectional view along lines 9-9 of FIG. 8 of an exhaust duct and motor of the present invention.

Figure 1:
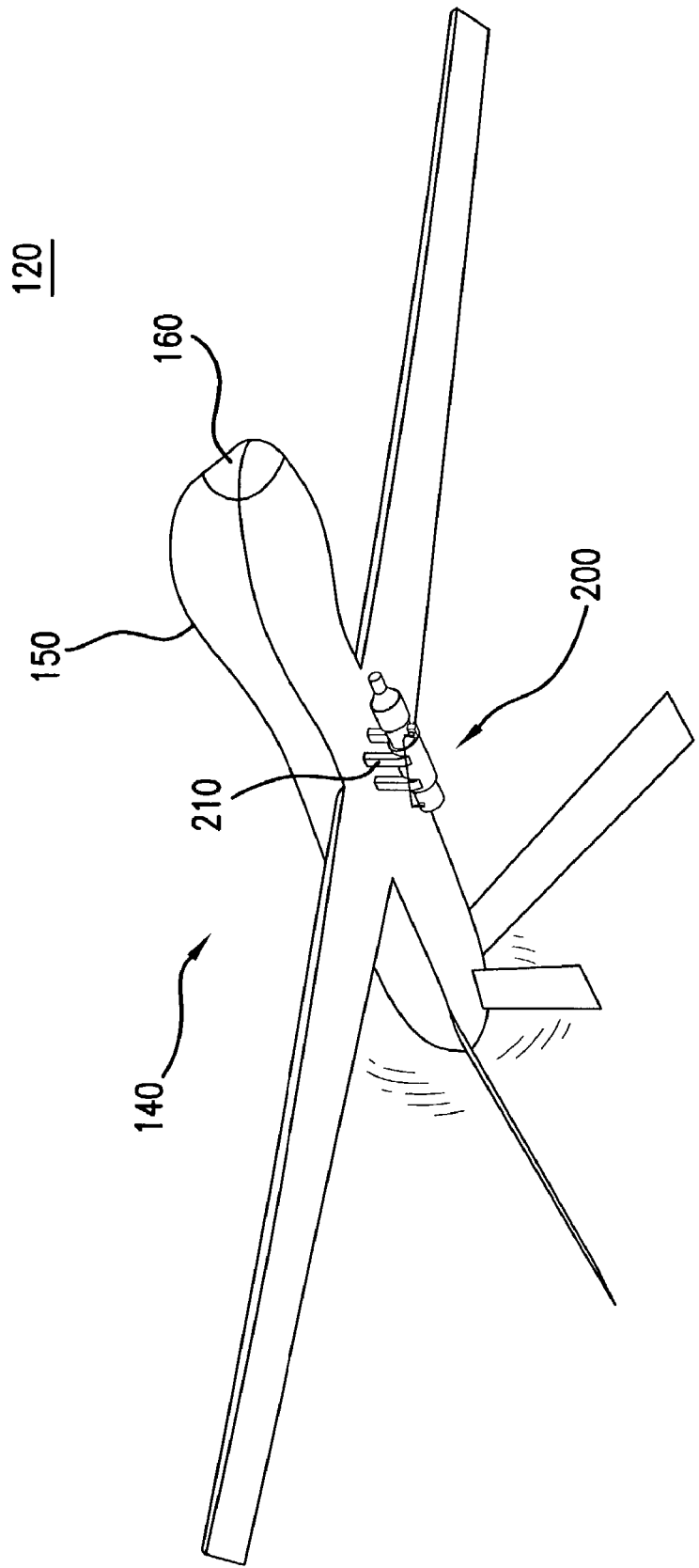
FIG. 1 is a perspective view of an exemplary collection device fastened to an aircraft.
Figure 2:
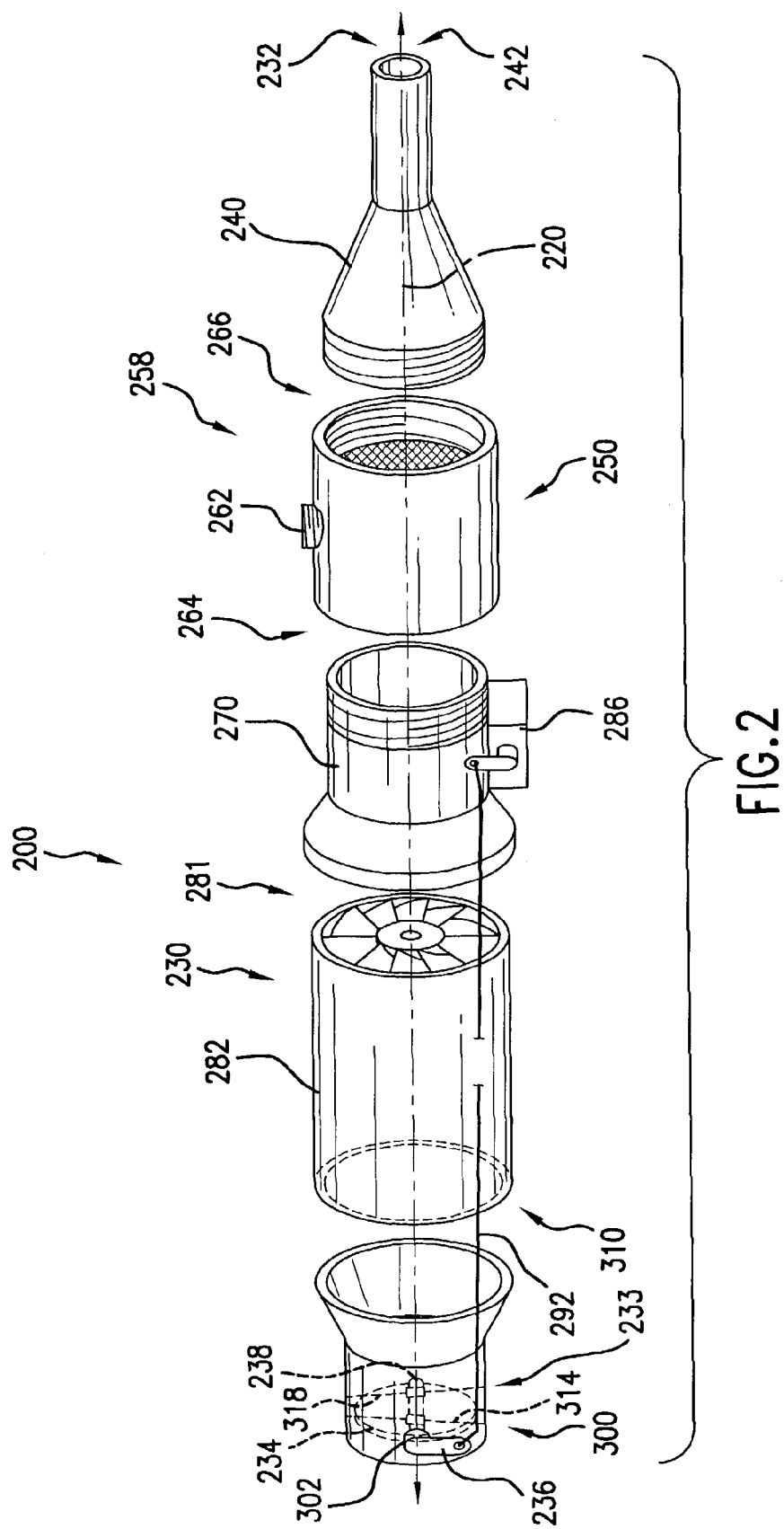
FIG. 2 is an exploded, perspective view of an exemplary collection device.

Referring to FIG. 1, one exemplary embodiment provides a collection device 200 that can be fastened to an aircraft 140 with mechanical fasteners 210. Alternatively, the collection device 200 can be received within a hollow nose cone 160 of the aircraft 140. The hollow nose cone 160 can be attached to a body 150 of the aircraft 140 in a conveniently releasable fashion using any suitable means such as mechanical fasteners. The aircraft 140 can be manned or unmanned, but preferably is a miniaturized unmanned aerial vehicle having a weight of less than 40 kilograms. Desirably, the aircraft 140 travels in an area 120 of interest to collect a substance, harmful or otherwise.

These substances can be harmful, such as poisonous gases, such as phosphine gas, mustard gas, VX gas, or chlorine gas. Other harmful substances that the collection device 200 can capture are pathogenic organisms, such as bacteria and viruses, toxic proteins such as botulinum toxin, ricin, aflotoxins, Staphylococcal enterotoxin B, anthrax bacteria and/or spores, small pox viruses, *Bacillus globigii* spores or other aerosolized pathogenic agents. Substances can also include biological particles such as bacteria, bacterial spores, fungi, fungal spores, mycoplasma, viral particles, and plant particles such as pollen grains. The collection device 200 can also collect non-harmful or relatively non-lethal substances such as ozone, particulates, smoke, dust, ash, or non-harmful organisms.

Although the collection device 200 is depicted mounted to an aircraft 140, it should be understood that the collection device 200 can be mounted to a variety of vehicles, such as boats, automobiles, personnel carriers, other land/water/air vehicles or robots, or maybe carried by a person. Alternatively, the collection device 200 can be used when stationary, optionally mounted using any suitable means such as mechanical fasteners to a support. Furthermore, the collection device 200 can collect substances, harmful or otherwise, from a variety of gases, including air. The collection device 200 desirably operates at a voltage of 24 volts with an average of 0.24 amps, however depending on available voltage, the present embodiment can be reconfigured to provide the same performance using different voltages.

Referring to FIG. 2 and FIGS. 4-9, a collection device 200 can include a body 230 forming a conduit 232 permitting the passage of gas therethrough. The body 230 can include a nozzle 240, a cartridge 250, a throat 270, a first motor 282, such as a fan, and an exhaust duct 300. Generally, the body 230 is a rigid, nonflexible material forming a defined, stable, fixed and/or unmoving conduit 232 throughout the entire length of the collection device 200. The nozzle 240 is connected to the cartridge 250 in a conveniently releasable fashion, and the cartridge 250, in turn, is connected to the throat 270 also in a conveniently releasable fashion. In one exemplary embodiment, the throat 270 and the nozzle 240 have male threads, which correspond to female threads on the cartridge 250. In addition, the throat 270 is connected to the motor 282 by any suitable means such as welding or adhesives. The motor 282, in turn, is connected to exhaust duct 300 using any suitable means such as adhesives or welds. Desirably, the cartridge 250, the throat 270, and the exhaust duct 300, can be made from any suitable material such as metal or plastic. Preferably, the cartridge 250, the throat 270, and the exhaust duct 300 are made from plastic, such as acetal or polycarbonate. The nozzle 240 forming an opening or inlet 242 can be made from any suitable material such as plastics or metals. In one exemplary embodiment, the nozzle 240 is constructed from aluminum.

The nozzle 240 can take a variety of sizes, such as varying diameter consistent with the velocity at which the collection device 200 travels during sampling to maintain approximately isokinetic sampling of the air. As an example, if the device 200 is traveling at slower speeds, the nozzle 240 may have a wider opening 242. On the other hand, if the collection device 200 is traveling at high speeds, the nozzle 240 can have a smaller opening 242. In one exemplary embodiment, this restriction permits the collection device 200 to be used in applications traveling at higher speeds, for example, 96-112 km/hour.

The cartridge 250 includes a first threaded end 264 and a second threaded end 266, preferably at opposing ends of the cartridge 250, and forms a cavity 252 for receiving a collection material 254. The cartridge 250 also includes a side 258 which forms an aperture 260 for receiving a plug 262. Desirably, the plug 262 has male threads which correspond to female threads formed on the walls of the cartridge 250 forming the aperture 260. The plug 262 forms a recess adapted to receive a tool, such as an Allen wrench, for removing the plug 262 from the cartridge 250 to permit adding or removing the collection material 254 into or from the cavity 252 of the cartridge 250. In addition, the cartridge 250 can have respective screens, namely a first and a second screen, 268 attached at respective first threaded end 264 and second threaded end 266 to secure the collection material 254 therein. In one desired embodiment, the cartridge 250 has an inner diameter of 2.1 centimeters.

The collection material 254 can be a variety of materials that entrap, absorb or adsorb substances. The collection material 254 may be a dry pack bed. The collection material can also be activated carbon, silica gel, porous polymer beads, magnesium silica absorbent, reactive paper, porous polymer beads, absorbent filters, a polymeric absorbent material, unsilianized glass wool, porous glass fiber, or an absorbent. If the collection material 254 is beads, desirably the beads are arranged in a pack bed inside of the cartridge 250.

In one preferred embodiment, the collection material 254 is a silica glass bead coated with a glygel formulation, i.e. a glygel coated bead 256. Preferred glygel formulations are disclosed in U.S. Provisional Application Nos. 60/375,790, entitled "Glycerol-Doped Aerogel Coatings as Biological Capture Media", and filed Apr. 16, 2002; and 60/375,905, entitled "Glycerol-Doped Aerogel Coatings as Biological Capture Media", and filed May 1, 2002, hereby incorporated by reference in their entireties.

Desirably, the glygel formulation is less than 1% of the weight of the coated beads, and about 1-2 percent of the total volume of the coated beads. The beads can be spherical in shape having a diameter of 425-600 microns. The glygel formulation coating generally has an average thickness of about 1 micron.

Generally, the silica beads are coated with the glygel formulation by initially adding about 200 g of preferably about 400 micron-600 micron, optimally about 500 micron diameter glass beads to preferably about 450-550 mL, optimally about 500 mL of about 1:1 MeOH:HCl solution and agitating for preferably about 1-5 hours, optimally about 1 hour. The beads are removed from the acid solution by filtration and rinsed with about 2 volumes of deionized water. Next, the beads are then added to preferably about 450-550 mL, optimally about 500 mL of 50% $H_2SO_4$ and agitated for preferably about 1-5 hours, optimally about 1 hour. The beads are removed from the acid solution by filtration, rinsed with about 10 volumes of deionized water, and then air dried overnight.

Subsequently, the about 200 g of glass beads are added to preferably about 450-550 mL, optimally about 500 mL of glygel coating solution and agitated for preferably about 160-200 minutes, optimally about 180 minutes. The beads are then removed from the solution by filtration. The coated beads are then spread evenly in a 9×13" pan and cured in a 100° C. oven for about 20 min. Desirably, the beads are stored dry at room temperature until they are used.

Any mass of silica beads can be used as long as the volumes of 1:1 MeOH:HCl solution, 50% $H_2SO_4$ solution, and glygel coating are adjusted accordingly. Desirably, if the glygel coated glass beads are used in a packed bed, the thickness of the bed ranges generally from 0.5-6 cm, preferably 0.5-2.5 cm, and optimally approximately 1 centimeter thick in, for example, the cartridge 250 used in conjunction with an UAV. Each glass bead is desirably about 400-600 microns in diameter.

When applied to conventional filter materials or air-collection matrix, the glygel formulation coating increases the trapping efficiency of the filter or matrix without adversely affecting other matrix properties. For example, assuming that a pressure drop is a necessary property, this must not be adversely affected by the coating in order to maintain adequate flow through the filter. The coating described herein may be used both to trap biological particles during air collection, and to provide a viability enhancer for bacteria during air collection. The coating can also be biocompatible for collection of air-borne biological particles and subsequent extraction and post-collection analysis protocols, and does not interfere with molecular analyses.

Alternatively, the cartridge 250 can be a disposable collection cassette. Instead of removing the beads 256 after each collection event, the cartridge 250 is removed and disposed of after extraction.

The throat 270 has threads to connect with the cartridge 250 in a conveniently releasable fashion. The throat 270 transitions the airflow from the cartridge 250 to the motor 282.

The collection can include a gas flow regulator, which can be a first gas flow regulator, a second gas flow regulator, or a combination thereof. In one exemplary embodiment as depicted in FIGS. 2 and 4-9, the first gas flow regulator 233 may be the valve 234 and the second gas flow regulator 281 can be the motor 282, although the term "first gas flow regulator" and "second gas flow regulator" are generally the same genus of a group that encompasses species including motors, dampers, caps and valves.

The motor 282 draws air, through the nozzle 240. Desirably, the motor can be a turbine, fan or blower, such as a motor sold under the trade designation MICRONEL D 361L by Micronel LTD of Zurich, Switzerland. Desirably, the motor creates a flow rate of 30 or more liters per minute, depending on the cross-sectional area and depth of the bead bed. With different fans, air pumps, and motors driving air through the bead beds, it is possible to achieve a large variety of desired flow rates and collection efficiencies. The preferred operating range for maximizing collection efficiency for particles of 0.5 μm-2 μm in cross sectional area is determined by the inlet air/gas velocity to the bead bed. For example, if 500 μm diameter beads are used for collecting aerosolized particles of 0.5 μm-2 μm aerodynamic diameter, the optimum inlet or face air/gas velocity for bead beds 0.5-2.5 cm in thickness is approximately 1.4 meters/second-2.5 meters/second. Each bed thickness has a corresponding optimum inlet air/gas velocity to maximize collection efficiency for different particle sizes and types.

The exhaust duct 300 is connected to the motor 282 by any suitable means such as welds, or adhesives, and has tapered walls to transition the airflow to the first gas flow regulator 233. Also, the exhaust duct 300 forms an aperture 302 for receiving a shaft 238, which is formed integrally with a handle 236. The shaft 238 serves as a mount for the first gas flow regulator 233 such as a valve 234. The first gas flow regulator 233 can be an internal device, such as a valve or damper, or an external device such as a cap that fits over the inlet 242 of the nozzle 240. The valve 234 can be a flapper valve, butterfly valve, ball valve, gate valve, or other type of flow control valve. Desirably, the valve 234 is a butterfly valve. It should be noted in one exemplary embodiment of the present invention that the first gas flow regulator 233 blocks by physically obstructing 70%, 80%, 90%, 95%, 99%, or up to and including 100% of the cross-sectional area of the conduit 232 to prevent any substantial amounts of gas from passing through the device 200. This prevents a substance from collecting on the collection material 254, thereby preserving the capacity of the collection material 254 to an area of interest 120. However, the term "blocks" does not include portions, e.g. blades, of a deactivated fan, blower, pump, or turbine positioned within a gas flow.

In a substantially cylindrical portion of the exhaust duct 300, between a portion defined by the tapering walls and the first gas flow regulator 233, at least one instrument 310, preferably a plurality of instruments, is positioned for measuring parameters for determining flow rates. The instrument 310 can be a single device, e.g. a flow meter or a thermistor, or can include a plurality of devices for determining airflow. In one preferred embodiment, the instruments are a first hot-wire anemometer or thermistor 314 and a second temperature sensor or thermistor 318. Desirably, the hot-wire anemometer is made from platinum, such as a platinum resistor, and operates at about 100° C. The hot-wire anemometer can be made with any number of either self-heated or externally heated devices such as platinum resistors, thermistors, or thermocouples. The energy required to maintain that temperature while the motor 282 is operating is measured as hereinafter described. The thermistor 318 is a passive element and measures the ambient air temperature, as hereinafter described. The thermistors 314 and 318 can be obtained from a variety of commercially available sources, such as Thermometrics, Inc. at 808 US Highway 1, Edison, N.J. 08817. Although it is contemplated that any gas may pass through the conduit 232 of the collection device 200, preferably the gas is air.

In addition, the collection device 200 also includes a second motor 286. Desirably, the second motor 286 is a servo motor, such as a servo motor sold under the trade designation HITEC HS-50, from HITEC RCD USA, 12115 Paine St. Poway, Calif., 92064. The second motor 286 is connected to the body 230, preferably the throat 270, using any suitable means as welds, bolts, screws, or adhesives. A pushrod 292 communicates the second motor 286 with the valve 234. A signal transmitted to the motor 286 permits positioning of the valve 234 via movement of the pushrod 292, thereby regulating airflow through the collection device 200.

In addition, the collection device 200 includes a system 100 for calculating airflow through the device 200 for determining the concentration of material collected. In one embodiment, the invention permits the calculation and storage of varying mass gas flow rates. Referring to FIG. 10, the system 100 can include at least one instrument 310, at least one microprocessor 510, a computer 590, and a motor 280. The at least one instrument 310 can include a variety of different flowmeters, or a plurality of devices, such as the thermistors 314 and 318 as described above. The at least one microprocessor 510 can be a single microprocessor, or a plurality of microprocessors 512 and 514 as hereinafter described. The computer 590 can receive information from the microprocessor 510, and is desirably a laptop computer. An optional feature of the system 100 is a feedback loop from the microprocessor 510 to the motor 280 to control the airflow through the collection device 200 as hereinafter described.

The system 100 can be used to implement a preferred performance process as depicted in FIG. 11. First, a user activates at least one motor to draw air into the device at 600. Desirably, the activation mechanism is a switch or a command signal from an external device that activates the first motor 282 to turn on a blower and second motor 286, which is a servo motor, to move the pushrod 292 to crank the handle 236 that rotates the shaft 238 and opens the flapper valve 234. Next, a timer in the microprocessor 510 is activated at 604. Furthermore, the first thermistor 314 is activated and heated to about 100° C. The second thermistor 318 is activated, measures the ambient air temperature, and creates a first signal, and meanwhile, the amount of energy required to maintain the first thermistor 314 at a constant temperature is measured and a second signal is created at 608. Afterwards, the first and second signals are amplified at 612. After amplification, the baseline voltage is removed from the first and second signals at 616. That being done, the microprocessor 510 calculates a temperature differential by subtracting a measured temperature signal value, namely from the temperature of the second thermistor 318, from a preset temperature value, namely the temperature of the first thermistor 314, at 620, and calculates a heat transfer coefficient from the temperature differential and at least one measured parameter such as energy consumption at 622.

The convective heat transfer co-efficient is determined from the following general equation:

$$q''=h*(Ts-Tinf)$$

where:

q" is the rate of heat transfer, (electrical power of the first thermistor 314);

h is the convective heat transfer co-efficient;

Ts is the temperature of the first thermistor 314; and

Tinf is the temperature of the medium (air) as measured by the second thermistor 318.

Because the voltage is needed to maintain the first thermistor 314 at a fixed resistance (which corresponds to Ts) and Tinf are measured, the equation is rearranged to $$h=q''/(Ts-Tinf)$$

where:

Ts is a constant resistance maintained by, e.g., a servo; and q"=voltage squared divided by resistance.

The actual converted voltage has a constant offset, (adjusted, e.g. by a variable resistor) so the equation for q" now is:

$$q''=(Vm-Vo)\hat{}2/Rth$$

where:

q" is the power needed to maintain the thermistor 314 at a set temperature (and resistance);

Vm is the measured voltage; (amplified and scaled in, e.g., an amplifier)

Vo is the offset voltage (a constant amplified and scaled in, e.g., an amplifier and set by, e.g., a variable resistor); and Rth is the constant resistance maintained by, e.g., a servo.

As an example, the microprocessor 510 can calculate q" using the known values of Vo and Rth and the measured value of Vm. This is done in 32 bit integer math with an 8 bit analog input to maintain accuracy.

The value of (Ts−Tinf) is calculated from the temperature of the unheated thermistor 318 (derived from the voltage that is, e.g., amplified, scaled, and converted to an 8 bit value in, e.g., the microprocessor 510). This 8 bit value is converted to (Ts−Tinf) directly by using a lookup table calculated off-line and loaded into the microprocessor ROM. This accommodates the non-linearity of the thermistor 318 circuit used to measure the air temperature. Ts is the constant temperature of the hot wire, as discussed above, and maintained by, e.g., a servo.

Dividing q" and (Ts−Tinf) in, e.g., the microprocessor 510 (using 32 bit integer math) yields an 8 bit result with h as a function of mass air flow.

Next, a correlation is created between the heat transfer coefficient and mass air velocity. Particularly, an exemplary collection device 200 having a diameter of 20.6 millimeters at the location of the thermistors 314 and 318 is placed in a wind tunnel and exposed at a chosen temperature, e.g. 24° C., to 22 different airflow rates ranging from 0.5-9 standard meters per second (corresponding to 10-180 standard liters per minute). The heat transfer coefficients at each of the 22 airflow rates is measured and plotted to correspond to each of the 22 airflow rates on a standard spreadsheet program, such as Microsoft EXCEL, sold by Microsoft Corp., of One Microsoft Way, Redmond, Wash. 98052-6399. Using the spreadsheet's curve fitting program, the following fourth order equation is generated representing the plotted data:

$$y=a*h\hat{}4+b*h\hat{}3+c*h\hat{}2+d*h+e$$

where h is the heat transfer coefficient;

and y is in liters/30 seconds, which can be divided by two at the point of final readout to give standard liters per minute; and the fitting constants for this particular device 200 at 24° C. are:

a=+1.03276e−6;

b=−3.67051e−4;

c=+4.91843e−2;

d=−2.37914e0; and e=+5.31656e+1, where h extends from 33 to 202 in the curve fit.

Using these 5 coefficients, a table, amplifier gains and offsets are calculated such that the normal flow rate of 30 standard liters per minute is about in the center of the range of the input voltage to the microprocessor 510 (e.g. 2.2 volts out of the range 0 to 5 volts) at normal room temperature (24° C.). The input voltage at 30 SLPM voltage can be quite a bit different at higher or lower temperatures. The current operational temperature range of the exemplary device above is from −10° C. to +40° C., but one of skill in the art can setup another device having different diameters to operate in any reasonable 50° C. temperature range by running the above correlation at a temperature within that chosen range.

To calculate the mass air flow rate, the following formula is used:

$$f = k^* v^* A$$

where:
f is mass flow rate expressed in liters per 30 seconds at standard temperature and pressure;
v is mass velocity;
A is the cross sectional area of the pipe
k* is a factor (1 in this case) to accommodate a non-uniform flow profile In one exemplary embodiment, the mass air flow rate at standard temperature and pressure can be calculated from 256 heat transfer values corresponding to the 256 inputted mass air flow rates at a chosen temperature. This data can be converted into a table and stored onto the microprocessor 510 as ROM. Once a given heat transfer coefficient is calculated at 622, the corresponding mass air flow rate value can be retrieved from the ROM look-up table in 624.

After retrieving the mass air flow rate value at 624, the mass air flow rate values are accumulated along with time counts at preset intervals, preferably 6 second intervals, in memory, at 628. Particularly, these accumulated values are stored in memory, desirably EEPROM, in the microprocessor 510 in standard temperature and pressure liters per 30 seconds, every 6 seconds, as a 32 bit number. The number of 6-second intervals is also accumulated to give the total time of collection to tenths of minutes. An advantage of EEPROM memory is that even if the collection device 200 impacts a hard surface, e.g. the aircraft 140 crashes, the first microprocessor 510 can be extracted from the wreckage, and plugged into an operational board, where the data can be retrieved.

That being done, the user can deactivate at least one motor by, e.g., turning a switch, to stop drawing air into the device 200 at 632. This action results in the reading out of the stored data at 636. Desirably, the data is read out at 6 second intervals. Afterwards, a user can extract stored data through a connector into, e.g. a laptop computer, from the microprocessor 510 at 640. The final results are divided by two to provide an output in tenths of liters per minute at standard temperature and pressure. The data output of cumulative flow-rate data, and optionally real-time data, can be 19200 baud for an 8-bit, 1 stop bit, odd parity. After extracting the data, the memory is cleared and the timer reset in the microprocessor 510 at 644.

Although this method has been described calculating the mass flow rate of air, one of ordinary skill in the art would readily appreciate that the above method could be used to calculate a mass flow rate or rates for other gases.

Optionally, the system 100 can include a feedback control loop to a motor 280. Particularly, the microprocessor 510, e.g. the microprocessor 512, can be preprogrammed with a mass air flow rate set point range. Comparing the retrieved mass air flow rate with the set point range allows a signal to be sent if the retrieved rate is outside the set point range. As an example, the microprocessor 512 can send a signal to the second microprocessor 514 that controls the first and second motors 282 and 286. Once the signal reaches the microprocessor 514, a signal can be sent to the relay 550 to alter the duty cycle of the power supply to the first motor 282 and/or a signal can be sent to the second motor 286. The first motor 282 can alter the blower speed of the motor 282 while the second motor 286 can throttle the valve 234. If controlling the air through the device 200 is desired, preferably the feed back control loop adjusts the first motor's 282 speed.

Figure 12:
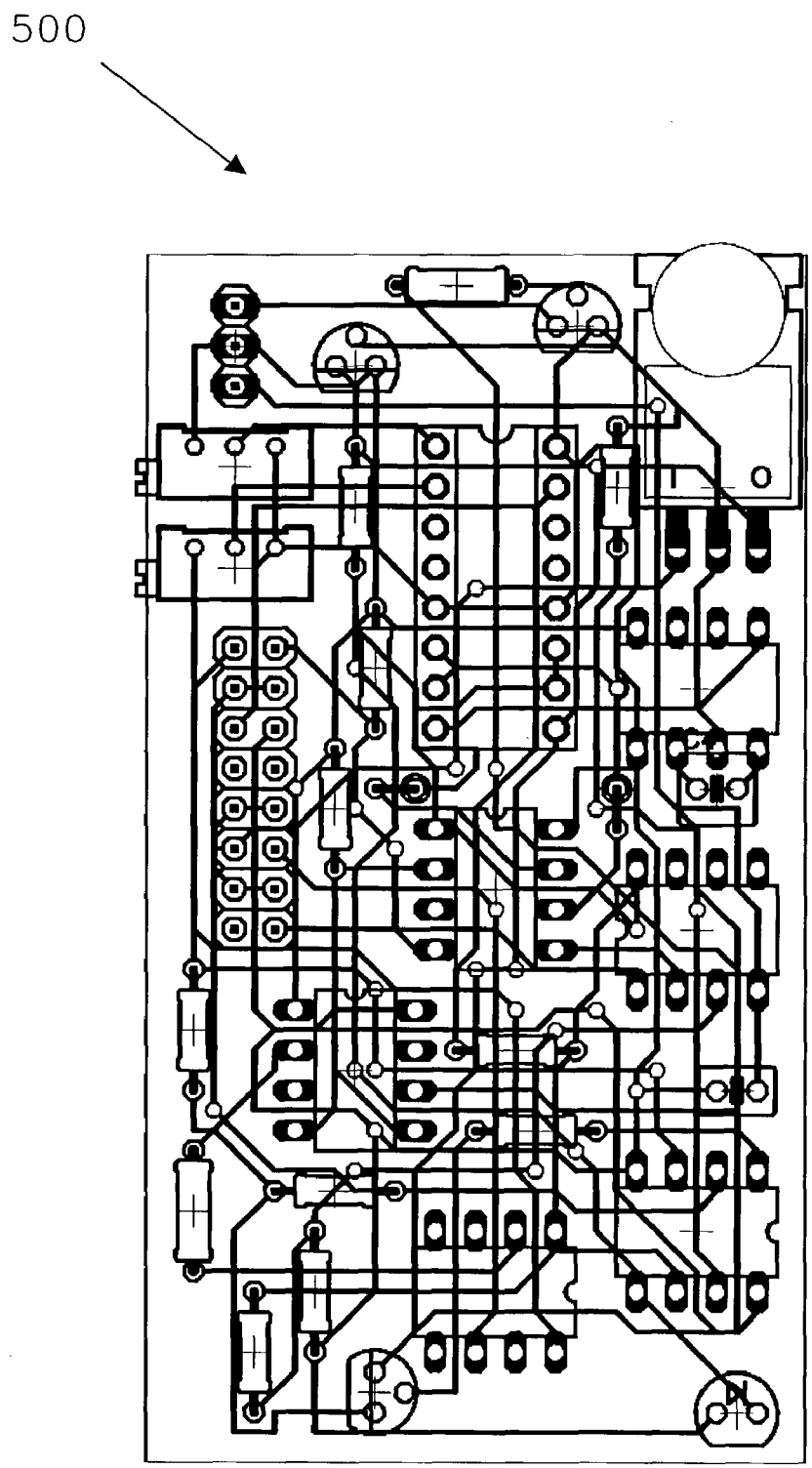
FIG. 12 is horizontal, plan view of a circuit assembly of the present invention.

Referring to FIG. 12, an exemplary circuit assembly 500 is depicted. Although one embodiment is depicted, those skilled in the art can contemplate other assembly versions suitable for use with the collection device 200.

Figure 13:
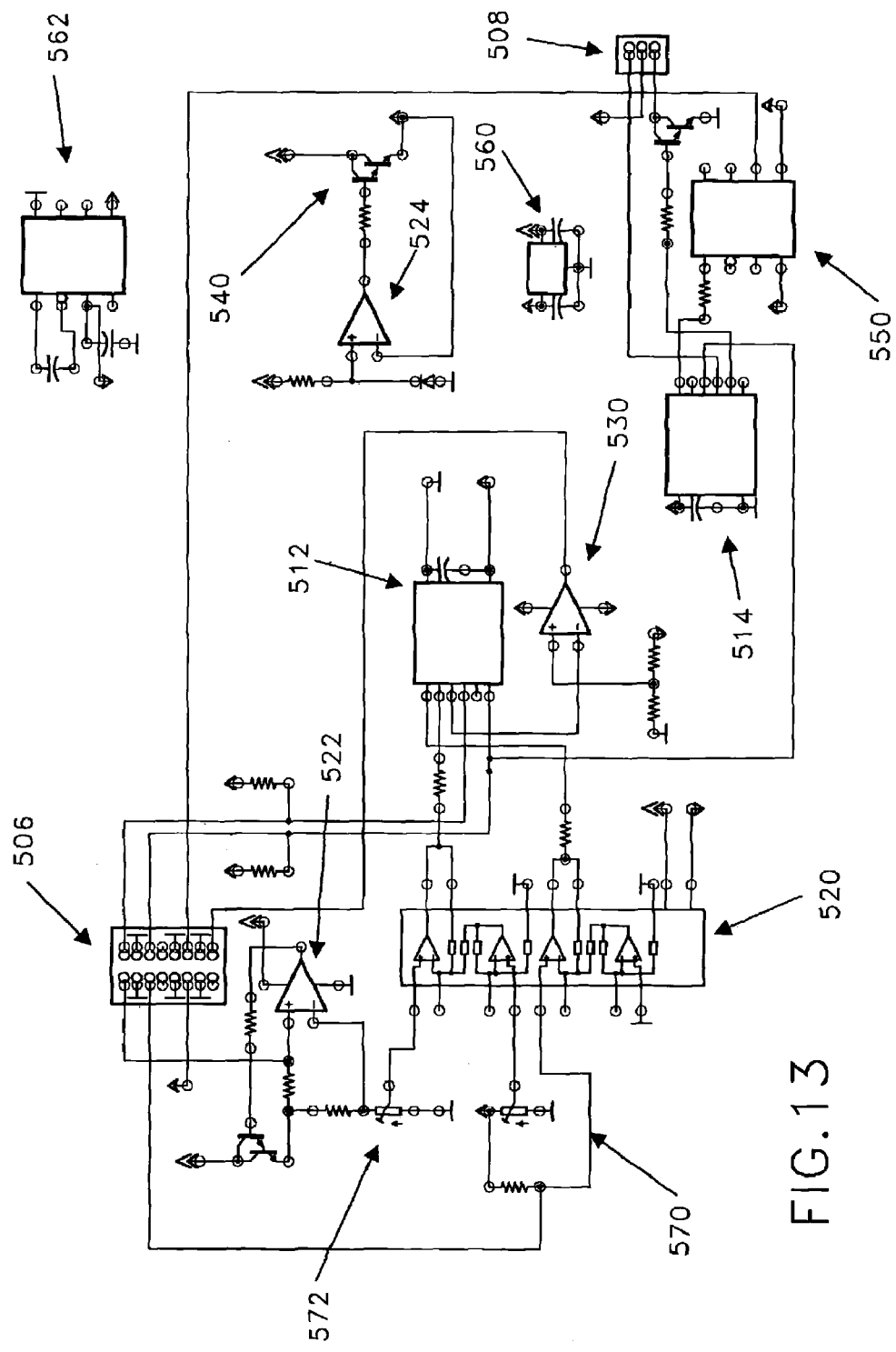
FIG. 13 is an exemplary circuit diagram for conducting, for example, the performance of FIG. 11.

Referring to FIG. 13, an exemplary circuit diagram is depicted. This exemplary embodiment of the present invention can include a first microprocessor 512 and a second microprocessor 514. Suitable microprocessors 512 and 514 can be obtained from Microchip Technology Inc., 2355 W Chandler Blvd, Chandler Ariz. 85224. This embodiment may further include a first amplifier 520, a second amplifier 524, a servo 522, an operational amp 530, a transistor 540, a relay 550, a voltage regulator 560, a voltage convertor 562, a first variable resistor 570, and a second variable resistor 572. A suitable first amplifier 520 can be an instrument amplifier (dual) obtained from Burr Brown at 6739 S Tucson Blvd., Tucson Ariz. 85706; suitable servo 522 or operational amp (dual), voltage regulator 560, voltage convertor 562, and 5 volt reference can obtained from National Semiconductor at 2900 Semiconductor Drive, Santa Clara, Calif. 95052-8090; and the relay 550 can be a solid state relay obtained from AROMAT a subsidiary of Matsushita Electrical Works at 224 Airport Pkwy, Ste. 100, San Jose, Calif. 95110. This embodiment may also include transistors sold under the trade designation NPN Darlington Transistors at Zetex PLC, Fields New Road, Chadderton Oldham OL9 8NP UK, as well as commercially available resistors, potentiometers, capacitors and connectors, such as the connectors 506 and 508.

In operation, gas, such as air, can enter the nozzle 240 drawn by the motor 282 and through the device 200 to exit the exhaust duct 300. Macroscopically, e.g. excluding turbulent eddies, the gas follows a linear, substantially uncurved, flow path 220, through the collection device 200, i.e. the conduit 232 forms a substantially linear path 220 for the gas. The gas can follow a linear path 220 just after entering the nozzle 240, exiting the nozzle 240, entering the cartridge 250, exiting the cartridge 250, entering the throat 270, exiting the throat 270, entering the motor 282, exiting the motor 282, entering the exhaust duct 300, and/or just before exiting the exhaust duct 300. In one preferred embodiment, the gas follows a linear flow path 220 just after entering the nozzle 240 and just before exiting the exhaust duct 300.

When, the gas, such as air, passes through the cylindrical portion of the exhaust duct 300, the mass flow rate can be calculated from parameters measured by the thermistors 314 and 318, as discussed above. Also as discussed above, while the collection device 200 is being transported to an area 120 of interest, the valve 234 can be closed preventing air from entering the nozzle 240 and the cartridge 250. This prevents the capture of materials onto the collection material 254 that is not of interest, thus extending the capacity of the collection device 200. Once the collection device 200 is positioned at a desired location 120, a signal can activate the motor 286 to open the valve 234 and the motor 282 to permit air to enter the nozzle 240 and pass through the collection device 200. Once the area 120 is sampled, the valve 234 can be closed permitting the transporting of the collection device 200 without gathering additional materials.

Figure 3:
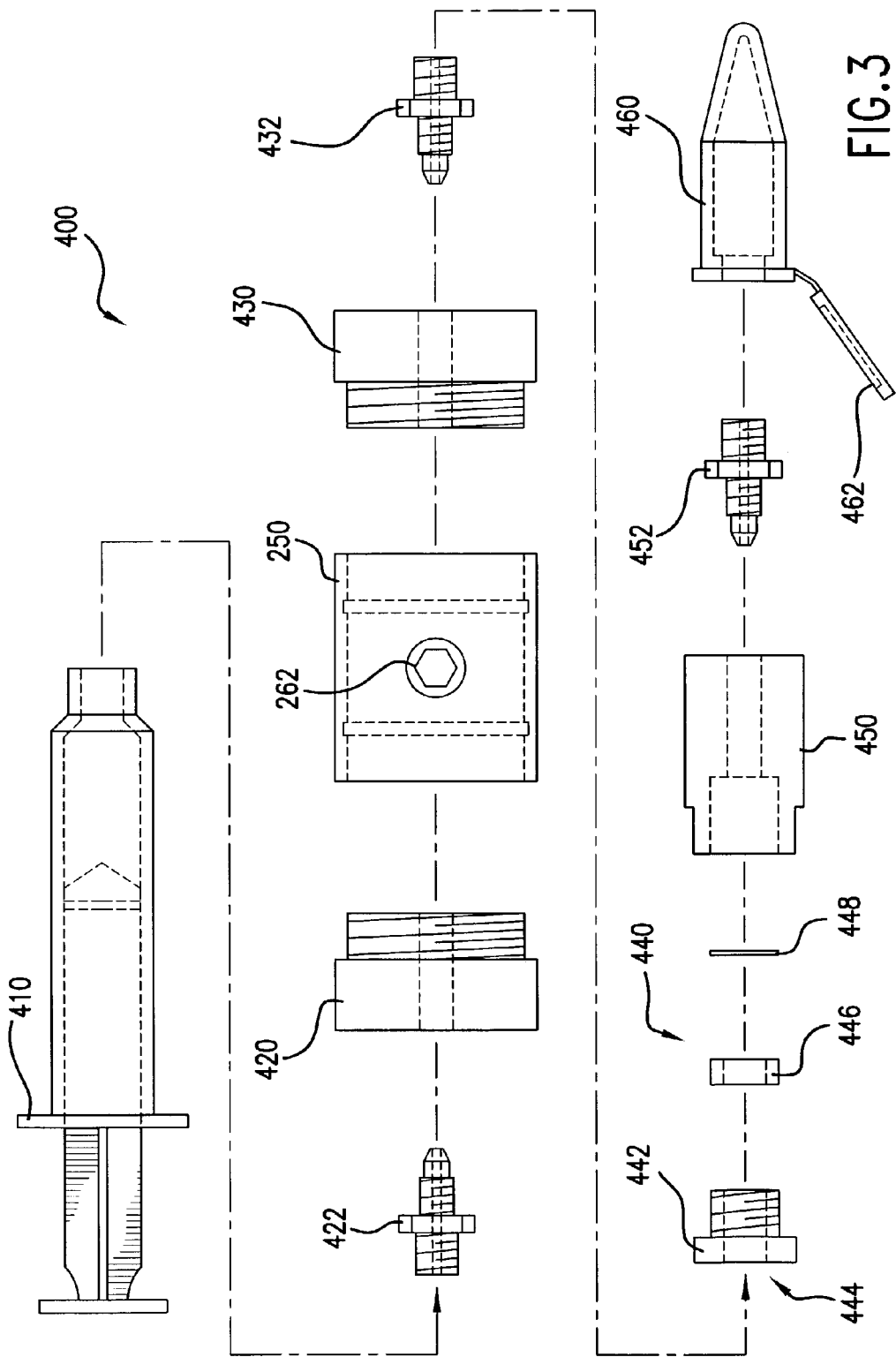
FIG. 3 is an exploded, perspective view of an exemplary sample retrieval system of the present invention.
Figure 4:
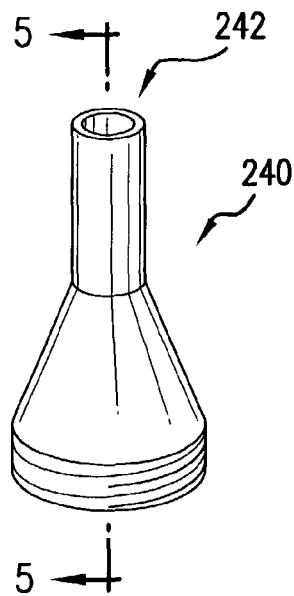
FIG. 4 is a perspective view of an exemplary nozzle of the present invention.
Figure 5:
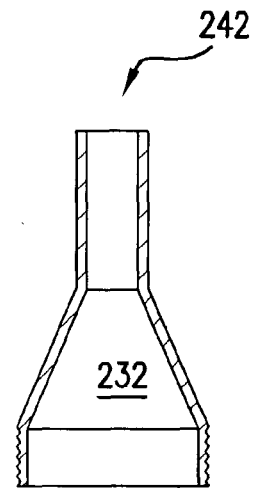
FIG. 5 is a cross-sectional view along lines 5-5 of FIG. 4 of an exemplary nozzle of the present invention.
Figure 6:
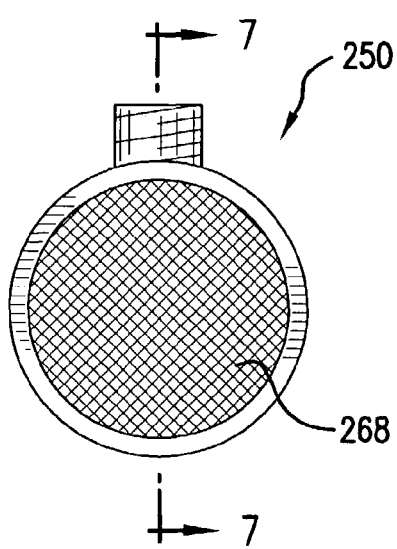
FIG. 6 is an elevational, end view of an exemplary cartridge of the present invention.
Figure 7:
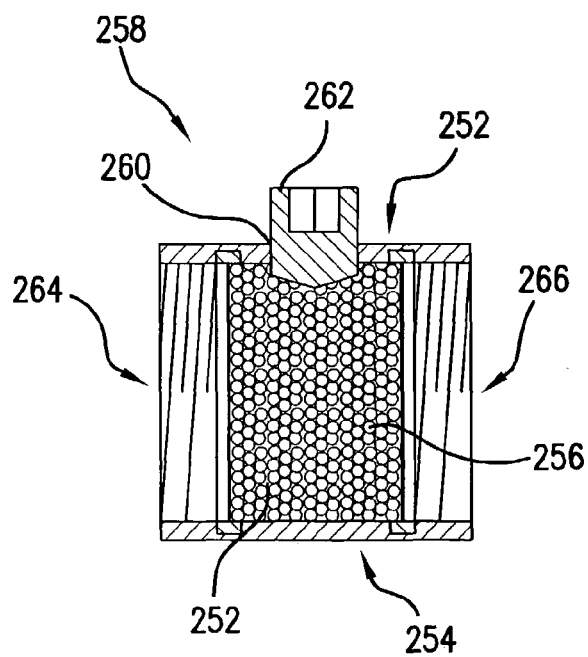
FIG. 7 is a cross-sectional view along lines 7-7 of FIG. 6 of an exemplary cartridge of the present invention.
Figure 10:
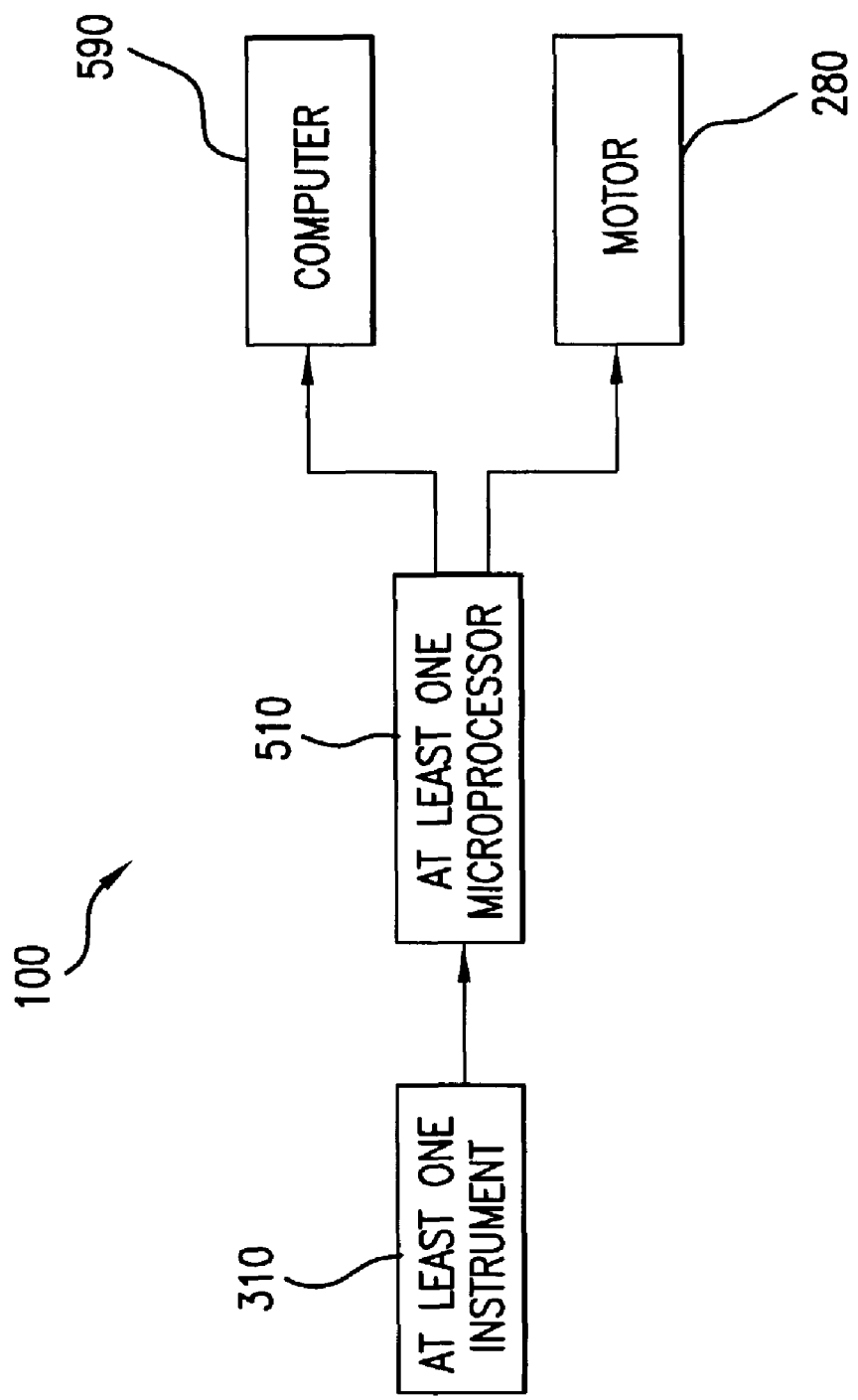
FIG. 10 is a block diagram illustrating a system implementing a preferred embodiment of the present invention.
Figure 11:
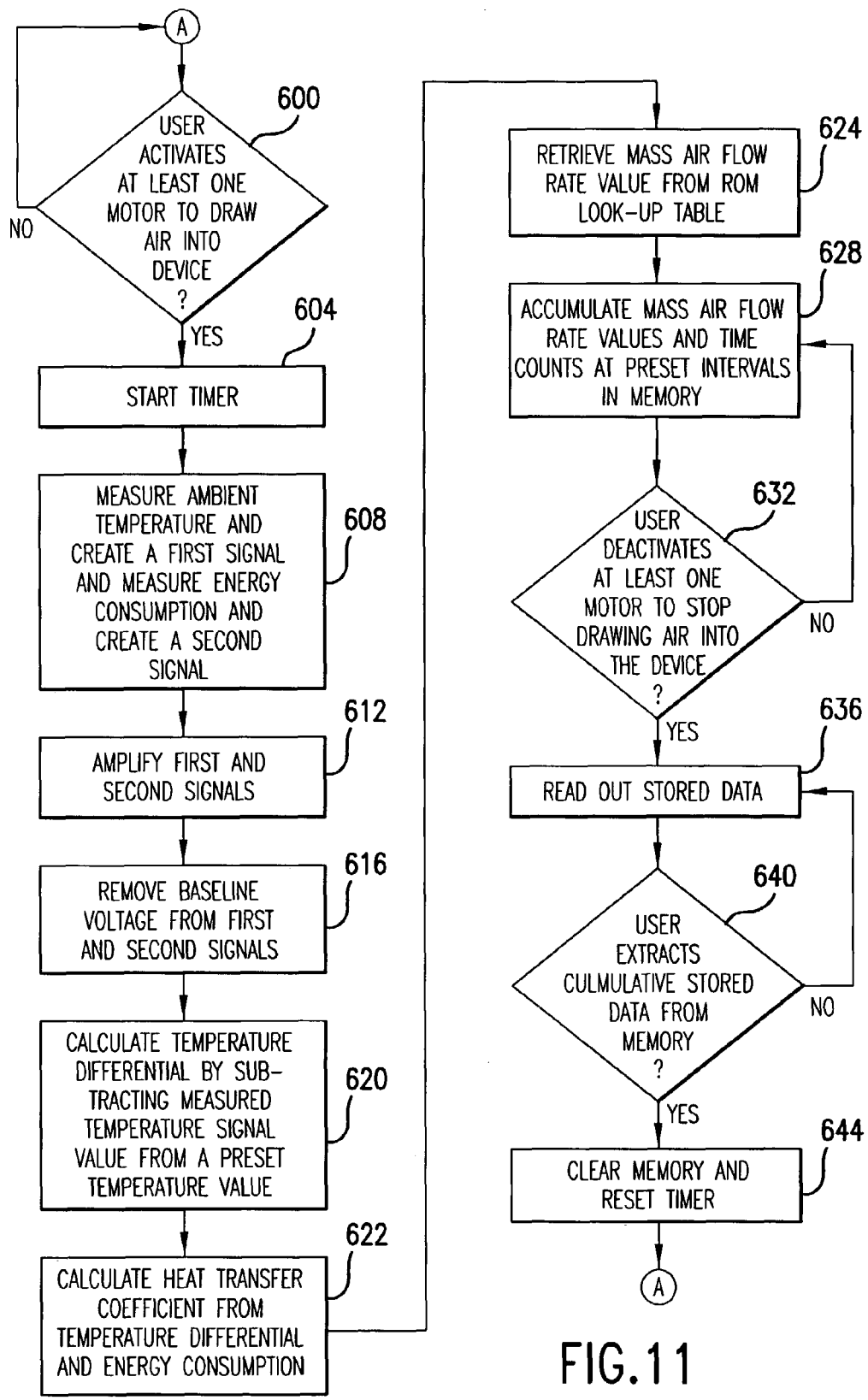
FIG. 11 is a flow diagram illustrating a preferred performance of the system of FIG. 10.

Once the sampling is completed, a substance can be retrieved from the collection material 254. The retrieval system 400 or method of the present invention can isolate the cartridge 250 and its collection material 254 to permit the retrieval of the substance while minimizing the handling required by a user. This is particularly beneficial if the substance is hazardous. Referring to FIG. 3, a retrieval system 400 includes a syringe 410, a first adapter 420, a first fitting or luer 422, a cartridge 250, a second adapter 430, a second fitting or luer 432, a filter assembly 440, a third fitting or luer 452, and a collection vessel 460. It should be understood that the term "adapter" encompasses the terms "fitting" or "luer" when such are attached to a cartridge 250. The filter assembly 440 can include an end piece 442 forming an aperture 444, a retainer 446, a filter 448, and a housing 450. The retrieval system 400 can include at least one adapter, preferably two adapters 420 and 430, and at least one fitting, and preferably three fittings or luers 422, 432, and 452. Preferably, the retainer 446 is a ring for securing the filter 448 within the housing 450. The filter 448 can exclude particles from 0.1-5 microns, preferably from 0.5 microns and larger. The collection vessel 460 can also include a lid 462.

After retrieving the collection device 200, if applicable, the collection device 200 can be unfastened from the aircraft 140. To isolate the cartridge 250, the nozzle 240 can be removed by unscrewing the nozzle 240 from the cartridge 250. In turn, the cartridge 250 can be unscrewed from the throat 270. Once removed, the adapters 420 and 430 can be attached to either end of the cartridge 250. The luers 422 and 432 attach to respective adapters 420 and 430 and permit the attachment of different size syringes and filtration units for the entrapment of biological samples that are rinsed off the cartridge beads. Suitable solvents for rinsing off the beads include phosphate buffered saline (PBS), water, TRITON-X 100 surfactant in water or PBS, sodium dodecyl sulfate in water or PBS, or similar buffered aqueous solutions containing surfactants or other agents for removing impacted particles from the bead bed. Attached to the luer 432 is the filter assembly 440, which in turn has the luer 452 attached at an opposing end and coupled to the collection vessel 460. The luers 422, 432, and 452, the adapters 420 and 430, the end piece 442, and the collection vessel 460 secure to adjacent pieces in a conveniently releasable fashion, preferably by threaded connections as depicted.

After the system 400 is assembled except for the syringe 410, the syringe 410 can be filled with a solvent and coupled to the luer 422. Depressing the plunger on the syringe 410 ejects the solvent to wash the collection material 254 inside the cartridge 250 to wash the hazardous material off the collection material 254 to the filter assembly 440. The hazardous material is trapped on the filter 448 while the solvent is collected in the collection vessel 460. After washing the collection material 254, the luer 432 can be separated from the adapter 430 and the collection vessel 460 can be separated from the luer 452. This sub-assembly surrounding the filter assembly 440 can be washed with a second solvent, such as deionized or distilled $H_2O$, by attaching a second syringe to the luer 452 and placing a test tube or vial adjacent to the luer 432. Ejecting the second solvent from the second syringe washes the hazardous material from the filter 446 and into the test tube or vial for analysis. The advantage of the two-step washing procedure is that the final sample can be concentrated and ready for polymerase chain reaction (PCR) analysis or other assays.

As an example, using a relatively large volume (e.g. 5 milliliters) rinses spores or other hazardous material off the collection material 254 onto the filter 448. Back rinsing with a smaller volume, e.g. 50 microliters, rinses spores or other hazardous material off the filter 448 for testing.

Alternatively, the biological substances can be extracted from the beads using a bead-beating apparatus.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all cited applications, patents and publications is hereby incorporated by reference.

EXAMPLES

Collection Device

One exemplary collection device of the present invention weighs no more than 0.5 kilograms. The flow rate and collection efficiency of this collection device is tested at an air speed of 64 kilometers per hour by attaching the device to the nose cone of a UAV and placing the entire assembly in a wind-tunnel where known concentrations of biological particles are introduced. During one such test, the device is exposed to ovalbumin aerosol for 10 minutes and has nearly a 100% collection efficiency. In another test, the device exhibits a 70% collection efficiency for aerosolized *Bacillus globigii* spores. Further, the coating on the beads in the collection cartridge enhances the survivability of collected vegetative prokaryotic cells to permit post-collection plating studies or DNA analysis.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A device for sampling air at a selected location for particulates suspended in the air comprising:
   a tube having an inlet with an inlet area and an outlet;
   a collection bed in the tube downstream of the inlet, said collection bed having a cross-sectional area greater than said inlet area;
   an exhaust fan in the tube downstream of the collection bed for drawing a stream of air through the collection bed causing particles entrained in the stream to deposit in the collection bed, and
   a flow regulator in the tube adjacent to the outlet for opening the outlet to allow the stream of air to develop in the tube at the selected location.

2. The device of claim 1 wherein a controller is provided to remotely open and close the flow regulator and to control the speed of the exhaust fan.

3. The device of claim 1 wherein the inlet comprises a nozzle having a diverging portion adjacent to the collection bed.

4. The device of claim 3 wherein the diverging portion has an inlet end configured as a cylindrical tube of a diameter less than an end of the nozzle.

5. The device of claim 4 wherein a controller is provided to remotely open and close the flow regulator and to control the speed of the exhaust fan.

6. The device of claim 5 further including a sensing arrangement for measuring parameters indicative of the flow rate of the air stream downstream of the exhaust fan.

7. The device of claim 6 wherein the sensor arrangement comprises thermistors which are connected to a microprocessor to determine temperature deviations from a selected level in order to control the speed of the exhaust fan.

8. The device of claim 7 further including a coupler for attaching the device to an aircraft.

9. The device of claim 1, the collection bed having a longitudinal axis, said collection bed comprising a plug that is removable from said collection chamber along an axis orthogonal to the longitudinal axis.

10. The device of claim 9, wherein the collection bed is removable from said device, the collection bed is configured to be attached to a syringe for flushing a particulate from the collection bed into a receptacle removeably attached to the collection bed, wherein the syringe and the receptacle are attached to opposite ends of the collection bed.

11. The device of claim 10, wherein thermistors are mounted in an opening of the outlet downstream from the exhaust fan.

12. A system for collecting airborne materials, comprising:

a conduit defining a flow path having an inlet with an inlet area;

a gas valve regulator configured to control passage of gas along said flow path; and a collection chamber positioned in said flow path downstream from said gas valve regulator, said collection chamber having an inlet and an outlet along a longitudinal axis and an additional opening, the inlet of said collection chamber having a cross-sectional area greater than the inlet area of said conduit, said collection chamber enclosing a plurality of beads coated with a glygel formulation, said collection chamber comprising a plug insertable into the opening that is removable from said collection chamber, thereby allowing for the addition or removal of the plurality of beads from the collection chamber through the opening;

wherein when said gas valve regulator allows gas to pass through said conduit along said flow path, substances suspended in said gas associate with said collection material for later retrieval and analysis.

13. The system of claim 12, said collecting chamber further comprising first and second screens configured to allow air to pass through said collection chamber and to contain said plurality of beads therebetween.

14. The system of claim 12, wherein said regulator comprises a first regulator, and said system further comprises a second regulator positioned in said flow path downstream of said collection chamber configured to draw a stream of gas through the collection chamber.

15. The system of claim 12, wherein said second regulator is an exhaust fan.

16. The system of claim 12, further comprising a controller configured to control at least said first and second regulators based on at least a flow rate of gas along the flow path.

17. The system of claim 12, further comprising at least one detector positioned in said flow path, said at least one detector configured to detect at least one characteristic of gas along said flow path.

18. The system of claim 12, wherein the collection chamber is removable from said system, the collection chamber is configured to be attached to a syringe for flushing a particulate from the collection chamber into a receptacle removeably attached to the collection chamber, wherein the syringe and the receptacle are attached to opposite ends of the collection chamber.

19. A flying pathogen collection device, comprising:

an aircraft;

a conduit having an inlet with an inlet area connected to said aircraft and defining a flow path;

a gas valve regulator configured to control passage of gas along said flow path; and a collection chamber positioned in said flow path downstream from said gas valve regulator, said collection chamber having an inlet and an outlet along a longitudinal axis and an additional opening, the inlet of said collection chamber having a cross-sectional area greater than the inlet area of said conduit, said collection chamber enclosing a plurality of beads coated with a glygel formulation, said collection chamber comprising a plug insertable into the opening that is removable from said collection chamber, thereby allowing for the addition or removal of the plurality of beads from the collection chamber through the opening;

wherein when said gas valve regulator allows gas in the vicinity of said aircraft to pass through said conduit along said flow path, substances suspended in said gas attach to said collection material for later retrieval and analysis.

20. The system of claim 19, said collecting chamber further comprising first and second screens configured to allow air to pass through said collection chamber and to contain said plurality of beads therebetween.

21. The system of claim 19, wherein said regulator comprises a first regulator, and said system further comprises a second regulator positioned in said flow path downstream of said collection chamber configured to draw a stream of gas through the collection chamber.

22. The system of claim 19, wherein said second regulator is an exhaust fan.

23. The system of claim 19, further comprising a controller configured to control at least said first and second regulators based on at least a flow rate of gas along the flow path.

24. The system of claim 19, further comprising at least one detector positioned in said flow path, said at least one detector configured to detect at least one characteristic of gas along said flow path.

25. The device of claim 19, wherein the collection chamber is removable from said device, the collection chamber is configured to be attached to a syringe for flushing a particulate from the collection chamber into a receptacle removeably attached to the collection chamber, wherein the syringe and the receptacle are attached to opposite ends of the collection chamber.

* * * * *